United States Patent [19]

Wilson et al.

[11] Patent Number: 4,874,611

[45] Date of Patent: Oct. 17, 1989

[54] MICROENCAPSULATED ANT BAIT

[75] Inventors: Wilfred W. Wilson, Brazoria; Sotiros C. Polemenakos; J. Larry Potter, both of Lake Jackson; Donald J. Mangold, San Antonio; William W. Harlowe, San Antonio; Herman W. Schlameus, San Antonio, all of

[73] Assignee: The Dow Chemical Company, Midland, Mich.

[21] Appl. No.: 129,503

[22] Filed: Dec. 7, 1987

Related U.S. Application Data

[62] Division of Ser. No. 746,896, Jun. 20, 1985, abandoned.

[51] Int. Cl.$^4$ .................. A01N 25/08; A01N 25/28; B01J 13/02
[52] U.S. Cl. ................. 424/410; 264/4.4; 424/84; 424/408; 424/455; 424/456; 424/492; 428/402.22
[58] Field of Search ............... 428/402.22; 424/84, 424/408, 455, 456, 492, 410

[56] References Cited

U.S. PATENT DOCUMENTS

| | | | |
|---|---|---|---|
| 3,160,686 | 12/1964 | Doyle et al. | 264/4 |
| 3,310,612 | 3/1967 | Somerville, Jr. | 264/4 |
| 3,389,194 | 6/1968 | Somerville, Jr. | 264/4 |
| 3,464,926 | 9/1969 | Vandegaer et al. | 424/419 X |
| 3,780,195 | 12/1973 | Balassa | 428/402.22 X |
| 3,917,825 | 2/1976 | Harris | 514/110 |
| 3,966,848 | 6/1976 | Schrider et al. | 558/162 |
| 4,107,292 | 8/1978 | Nemeth | 424/419 X |
| 4,160,824 | 7/1979 | Inazuka et al. | 424/84 |
| 4,375,481 | 3/1983 | Kuwabara et al. | 426/104 X |
| 4,707,355 | 11/1987 | Wilson | 424/84 |

FOREIGN PATENT DOCUMENTS 221685 6/1974 Fed. Rep. of Germany ........ 424/84

OTHER PUBLICATIONS

*The Pesticide Manual*, Seventh Edition, Published by The British Crop Protection Council (1983), p. 3050.
F. W. Billmeyer, Jr.: *Textbook of Polymer Science*, Second Edition, John Wiley & Sons, Inc., New York (1971), pp. 500 & 501.
P. Karlson: *Introduction to Modern Biochemistry*, Second Edition, Academic Press, Inc., New York (1965), pp. 53 & 54.
Tiny Capsules: Big Guns In Pest War, Chemical Week, vol. 106, No. 12, Mar. 25, 1970, pp. 32 & 33.

*Primary Examiner*—Richard D. Lovering
*Attorney, Agent, or Firm*—D. Wendell Osborne; Joseph T. Majka

[57] ABSTRACT

A method of manufacture and the product made thereby are set forth; in the preferred and illustrated embodiment, a core including an insect poison is encapsulated by shell material melting and hardening for encapsulation. The core is primarily soybean extract mixed with DURSBAN ® insecticide, an example of a toxicant. The surrounding shell or encapsulation is formed by melt extrusion of shell material. The surrounding shell encloses the core material to form an impervious shell. The surrounding shell includes soy protein as an insect attractant mixed in gelatin or poly(-vinyl alcohol). A gelling agent such as carrageenan and the attractant were added to the shell. The beads formed by the melt extrusion encapsulation has sufficient shell strength to enable mechanical handling for dispensing, are resistant to water, do not bleed from the inside to the outside, and yet can be penetrated by the insect.

11 Claims, No Drawings

MICROENCAPSULATED ANT BAIT

CROSS-REFERENCE TO RELATED APPLICATION

This is a division of application Ser. No. 746,896 filed June 2, 1985, now abandoned.

BACKGROUND OF THE DISCLOSURE

This disclosure is directed to an improved bead form insecticide. It is particularly intended for use with fire ants. A colony of fire ants is protected by the imposition of tasters between the ants which forage in the field and the queen which propagates the life of the colony. Thus, insecticides which require ingestion may very well kill the ants of the colony, but rarely, if ever, reach the queen; the colony may thus be reduced in population, but it will typically not be eradicated.

A desirable form of poison for fire ants is Dursban ® insecticide.

Fire ants typically will not carry exposed insecticidal material into the colony. Rather, it must be in a bait form where the fire ants carry it into the colony and thereafter penetrate it to ingest the carrier and the insecticide. Encapsulation prepares the insecticide for ant removal into the colony. Ideally, the foraging ants pick up the encapsulated active ingredient and carry it into the colony where the microcapsule is penetrated and the core containing the soybean oil and the active ingredient is ingested.

The encapsulation requirements impose a somewhat delicate balance. The surrounding shell about the core must be sufficiently tough to be mechanically handled from the time of manufacture, bagging, transportion and field dispersion. On the other hand, the shell must be sufficiently soft to enable the insect to penetrate it. Moreover, the shell must be impervious to the poison within; this means the shell must be attractive to the insect and yet not bleed so that the enclosed fumigant poison leaks through. Moreover, the shell must be of sufficient thickness in conjunction with toughness to assure the mechanical handling mentioned above. The balance of factors relating to shell fabrication including size requirements are fully met with the melt extrusion processes for microencapsulation as described below in detail.

This process is to be distinguished from microencapsulation accomplished via interfacial polycondensation procedures typically involving two part polymer systems and a liquid carrier. Such processes typically form a shell having a polyamide-polyurea mixture. Other polymer systems for interfacial polymerization formed shells are known. It is relevant to the present disclosure to note that a shell around the core is ideally impermeable and impervious to the core material being primarily an attractant for the insect species. Moreover, the surrounding shell must be reasonably rugged and durable, typically capable of storage in conventional conditions for months and wherein the shell is able to mechanically protect the stored core within without detrimental deterioration during storage. When dispersed, it may well be required to withstand rugged weather conditions including contact with water for a period of time. It is particularly desirable that the capsule have a size of about 300 to about 700 microns with sufficient insecticide within to enable the targeted fire ants species to pick up such capsules. The process of this disclosure sets forth a procedure where a proper shell can be formed around the core which shell has the requisite mechanical characteristics, is impervious to the core, and is not water soluble, is able to mechanically survive from fabrication through dispersal and yet is able to be broken open by the insect.

The present disclosure contemplates use of fire ant toxicants which when ingested will eradicate an insect colony.

One important feature of the insecticide formed by this process is a core payload in the range of about 60-70%. If desired, the core payload can be slightly increased, but it is believed that the payload range of about 60-70% is particularly desirable. This enables the core to adequately contain sufficient insecticide for fire ant eradication.

Many objects and advantages of the method of manufacture and the product formed thereby will be noted on review of the description of the preferred embodiment set forth here below.

DETAILED DESCRIPTION OF THE PREFERRED EMBODIMENT

The materials which comprise the core will be described first, the materials used in fabrication of the surrounding shell will be described secondly, and the method of manufacture will be set forth thirdly. In some degree, the methods of manufacture imposes certain physical requirements on the selection of materials. The product made by the process described below will thereafter be set forth and a number of mechanical features of this product will likewise be described. It should be kept in mind that these features enable the particular insecticide to operate successfully as a fire ant poison of significant potency.

The core of the microencapsulation product is preferably formed of two parts. First, an effective insecticide is selected as the active ingredient in the formulation. The most effective such material is chlorpyrifos sold under the trademark of DURSBAN ® by The Dow Chemical Company.

This is mixed to form the core material which is preferably a food attractant. One food attractant is soybean oil. Typically, the extracted material is primarily oil; moreover, other grain oil extracts will suffice, one being exemplified by extracts of cottonseed oil. A mixture is formed with the attractant and toxicant. The approximate ratios are calculated so that the smallest microencapsulated bead has sufficient toxicant therein to be insecticidally effective; this typically requires in the range of up to about two percent DURSBAN ® in the finished product. Typical specimens are given in Table 1 below which tabulates that approximate percentage of DURSBAN ® in the completed microencapsule. The mixture of toxicant and attractant should likewise be extrudible through an orifice of very small diameter perhaps in the range of about a one mm. diameter.

FIRST EXAMPLE

The shell material is formed of a mixture to obtain the physical characteristics which would be described herein below. As a first example, one shell is type B gelatin, a material obtained from alkali treated raw materials. It is strongly hydrophilic, typically absorbing many times its weight in water. It is mixed with carrageenan. This is a colloid, typically extracted from certain red marine plants to form a mixture of polysaccharide fractions. In like fashion, it is hydrophilic. Another portion of the shell is soybean protein. One shell composition is 88.9% gelatin, 6.7% carrageenan, and 4.4% soybean protein. The precise percentages given describe a specific embodiment of shell composition for use in fabrication of the microencapsulation described below. For ranges, the soybean protein should be sufficient to serve as an external attractant to the target species. This typically requires from about 2% to a maximum of about 8 or 9% in the shell. If the percentage is below this, it may be sufficiently dilute that it does not serve the attractive purpose while increasing above this range may weaken the shell mechanically. Sufficient carrageenan is required to accomplish gelling of the shell material during melt extrusion, and the range of about 5–15% is normally sufficient. The remainder of the material is gelatin.

Interestingly, the finished insect bait resembles a seed in the provision of a shell of protein (an attractant) around a promising core which is much more edible, being oil. The seed like similarity of the bait is sufficiently attractive by virtue of the surrounding shell that the bait will taste or smell sufficiently to be carried to the nest.

SECOND EXAMPLE

A second example for the shell composition is a mixture of poly(vinyl alcohol), a water soluble polymer. Physical characteristics of poly(vinyl alcohol) are in part dependent on the degree of polymerization and the degree of alcoholysis, factors which can be controlled during processing. A specific shell composition is 88.9% poly(vinyl alcohol) and the other constituents are similar to the example recited above to define a successful shell composition. The ranges of the shell constituents are similar to those given in example one of the shell composition material.

The food attractant in the shell composition is preferably soybean protein. Alternate food attractants include other rice or grain proteins characterized by being compatible with the shell composition materials and capable of forming a food attractant in the shell mixture not detracting from mechanical characteristics thereof. The food attractant must be appealing to the target insect species, as for example, attractive to the target species causing the foraging insects to carry the microencapsulation bead to their colony.

One method of manufacture of the insecticidal bait of this disclosure uses a centrifugal extrusion apparatus. Such a device is described in various U.S and foreign patents. The device uses a vertical feed line providing the flowable core material to a rotating head. The head includes a nozzle (one or more) radially directed to extrude a flow of the core material. The shell material is supplied through a larger, concentric flow line surrounding the vertical core material feed line.

The feed lines are stationary but the head rotates about an axis coincident with the feed lines. The two feed lines discharge into the head, the core material flowing into an elongate nozzle having a discharge orifice directed radially outwardly. The shell material flows to an annular orifice around the core material at the nozzle tip. The two orifices discharge a steady liquid flow, perhaps envisioned as spaghetti having a core surrounded by the shell material.

The head rotates at such a speed that the spaghetti extrudate is broken into pieces, more accurately, into droplets by the centrigual force. This can be controlled by variation of nozzle size, angular velocity, feed rates and the like. Thus, small beads are formed with surface tension of the liquid droplets defining spherical beads. The beads are sized within the range specified herein.

The beads are thrown from the rotating head to be collected, normally in a surrounding liquid bath or on a static powder bed. The beads are typically cooled in flight and also by the bed or bath. They are normally ready for use after drying.

Another examplary method of manufacture of the encapsulated insecticidal bait of this disclosure is use of the melt extrusion apparatus set forth in U.S. Pat. No. 3,389,194 and also 3,310,612. Additional microencapsulation description can be obtained from U.S. Pat. No. 3,160,686 and also 3,464,926. As exemplified in the '194 patent, the shell material is first heated to form a hot mix which hardens while suspended in a flowing carrier fluid. The carrier fluid is first heated to a temperature above the melting point of the shell material. The shell material is extruded into the flowing carrier fluid which is thereafter cooled, enabling the shell material to harden with cooling of the carrier fluid. The carrier fluid carries individual beads away in a rapid flow thereby enabling individual beads to harden without contact against other tacky beads. Thus, bead separation is assured as the shell hardens. In typical cases, the flowing carrier fluid is immisible or at least primarily so; it is flowed into a screen or sieve to retrieve the cooled beads from the carrier flow. Thus, the carrier fluid is conducted through a suitable down stream conduit and is cooled as it flows and is thereafter emptied into a collection container or vessel such as a sieve. The '194 patent describes one such system.

As shown in that reference, the core material is delivered through a first conduit emerging through a restricted orifice or opening surrounded by an outer concentric tube where the film material is likewise extruded. Thus, droplets of the core material are surrounded by film to form the beads. It is believed that beads in a range of about 350 to about 700 microns are desirable for fire ants. Such a size can be fabricated by the apparatus set forth in the '194 reference.

As was observed above, the shell is mechanically formed by cooling which is accomplished in the flowing carrier fluid substantially free of bead to bead contact. To this end, the shell material should have a selected melting temperature and hardens to a sufficient degree to enable subsequent handling on a specified temperature drop. A subsequent greater drop to ambient temperature may complete the gelling of the surrounding shell. That is, the shell may further harden with the subsequent processing. There is a desirable time rate temperature reduction and at this end, the transient time of the partially hardened bead in the carrier fluid as well as the temperature gradient of the fluid is likewise controlled by controlling flow velocity and temperature drop. Thus, the temperature of the shell material is reduced, but not too rapidly or too slowly, all for the purpose of forming the shell. In general terms, the carrier fluid is normally chemically nonreactive with the shell material. Ordinarily, the shell ingredients are water soluble. To the extent that some portion of the shell material is soybean protein, it is less miscible with water. Even if somewhat miscible, the liquid shell material in the hot melt processing, described herein, hardens relatively quickly in response to temperature reduction of the carrier fluid by counter current cooling from a heat exchanger. The core or filler material may or may not be hardened during operation of the melt extrusion process. Its viscosity may change little or significantly without detracting from the finished product.

The following mechanical characteristics are obtained from encapsulated insecticidal beads. Typically, the beads range from about 350–700 microns. The core typically is in the range of about 60 to about 70% by weight of the finished product. The surrounding shell is impervious to the soybean oil on the interior. This is particularly important in that the oil does not bleed through resulting in a loss of the toxicant. The lack of bleed through avoids insect inspection by foragers. Post fabrication handling steps including cooling and drying provide a relatively solid shell able to withstand the requirements necessary for manufacture and distribution. Thus, the completed shell is primarily impervious to the core material and yet it is made with sufficient attractant in the skin of the shell to cause foraging fire ants to pick up such beads and carry them to their colony. The beads are mechanically sound in that they can be fabricated, stored and thereafter dispensed through mechanical handling equipment. In the event that such beads were to fracture during shipment, the core material of a broken bead might well smudge the exterior of other beads and thereby repel or kill the foraging insect in the field. If this were to occur, the bead would not then be delivered into the colony where it is capable of accomplishing greater extermination.

Once the aqueous shell fabrication process has been completed and the shell has cooled to form a hard shell thereabout, the shell is water resistant in that water does not dissolve the shell or otherwise penetrate the shell, thereby destroying mechanical integrity or otherwise prematurely releasing the insecticide. This is particularly true in the event that the product, after fabrication, is broadcast by mechanical distribution equipment (tractor drawn or airborne) for dispersal across a field or pasture and thereafter lays on the ground subject to rain or dew accumulation. It may be hours or days before the bead is found by foraging fire ants. When they do find the bead, the prior exposure to water in the field does not prevent the microencapsulation bead from being carried by the foraging insect to the colony.

Table 1 below exemplifies several beads formed by this procedure. For descriptive purposes, the products forming the shell in examples one and two above were:

Gelatin—Dynagel, Type 150 Bloom
Carrageenan—Gelcaran HWG
Soybean Extract—Soy Bean Isolate Product (Pro-fam S792)
Poly(vinyl alcohol)—Elvanol 98-50, DuPont
Dursban ®—insecticide made by Dow Chemical Company

TABLE 1

| SHELL COMPOSITION | CORE MATERIALS | CORE % BY WEIGHT | DURSBAN % BY WEIGHT | SIZE IN MICRONS |
|---|---|---|---|---|
| Example 1 | .31% Dursban ® in Soybean Oil | 62.2 | .19 | 355-700 |
| Example 1 | .25% Dursban ® in Soybean Oil | 62.2 | .16 | 355-700 |
| Example 1 | .16% Dursban ® in Soybean Oil | 62.2 | .10 | 355-700 |
| Example 1 | .08% Dursban ® in Soybean Oil | 62.2 | .05 | 355-700 |
| Example 1 | .04% Dursban ® in Soybean Oil | 62.2 | .025 | 355-700 |
| Example 2 | .31% Dursban ® in Soybean Oil | 66.8 | .21 | 355-700 |
| Example 2 | .16% Dursban ® in Soybean Oil | 66.8 | .11 | 355-700 |
| Example 2 | .08% Dursban ® in Soybean Oil | 66.8 | .05 | 355-700 |
| Example 2 | .04% Dursban ® in Soybean Oil | 66.8 | .027 | 355-700 |

As desired, various surfactants may improve encapsulation of this soybean oil core. This may reduce the tendency of the oil to bleed through the surrounding shell which would make the product unattractive with toxicant exposed through the shell.

While the foregoing is directed to the preferred embodiment of the present invention, other and further embodiments of the invention may be devised without departing from the basic scope thereof, and the scope thereof is determined by the claims which follow.

What is claimed is:

1. A solid insecticidal bait comprising a generally spherical pellet of approximately 300 or more microns diameter having an enclosed core primarily made of a target insect attractant food, and mixed therein an insect toxicant in sufficient quantity for effective eradication, and including a surrounding polymeric water resistant shell impervious to the attractant food, said shell formed of poly(vinyl alcohol) or type B gelatin mixed with an attractant protein and gelling agent and wherein the core is up to about 70% by weight of the bait.

2. The bait of claim 1 wherein said shell includes about 4% soybean protein, about 6% carrageenan, and about 90% of either poly(vinyl alcohol) or type B gelatin.

3. The bait of claim 1 including a surfactant added in trace quantity to said core.

4. The bait of claim 1 wherein the toxicant is an ingestion poison.

5. The bait of claim 1 wherein the toxicant is up to about 2% by weight of said core.

6. The bait of claim 5 wherein the remainder of said core is edible soybean oil.

7. The bait of claim 5 wherein the bait includes up to about 2% by weight an ingestion poison and the remainder of said core is soybean oil, and said shell includes up to about 5% of soybean protein in a quantity sufficient to attract the target insect.

8. The bait of claim 7 wherein said shell includes about 4% soybean protein, about 6-7% carrageenan, and about 89-90% of either poly(vinyl alcohol) or type B gelatin.

9. The bait of claim 1 wherein the toxicant is oil soluble.

10. The bait of claim 1 wherein said food is primarily soybean oil.

11. The bait of claim 1 wherein the toxicant is chlorpyrifos.

* * * * *

UNITED STATES PATENT AND TRADEMARK OFFICE
CERTIFICATE OF CORRECTION

PATENT NO. : 4,874,611
DATED : October 17, 1989
INVENTOR(S) : Wilson et al.

It is certified that error appears in the above-identified patent and that said Letters Patent is hereby corrected as shown below:

On the title page, under "Inventors", last line, after "of" insert -- Texas --;

Col. 1, line 7, delete "June 2", and insert -- June 20 --;

Col. 1, line 27 "ingredient" has been misspelled;

Col. 4, line 10, "exemplary" has been misspelled.

Signed and Sealed this

Third Day of March, 1992

Attest:

HARRY F. MANBECK, JR.

*Attesting Officer*  *Commissioner of Patents and Trademarks*